United States Patent
Wilson et al.

(10) Patent No.: US 9,655,787 B2
(45) Date of Patent: May 23, 2017

(54) STACKED MOISTURE SENSING DEVICE

(75) Inventors: Richard R. Wilson, Arden Hills, MN (US); Douglas R. Oudekerk, Saint Paul, MN (US); Douglas P. Wilson, Madison, WI (US); Karla M. Fogel, Evanston, IL (US); Rebecca Neth Townsend, Bellevue, WA (US)

(73) Assignee: Covenant Ministries of Benevolence, Chicago, IL (US)

( * ) Notice: Subject to any disclaimer, the term of this patent is extended or adjusted under 35 U.S.C. 154(b) by 1060 days.

(21) Appl. No.: 12/950,569

(22) Filed: Nov. 19, 2010

(65) Prior Publication Data

US 2012/0130330 A1    May 24, 2012

(51) Int. Cl.
*A61F 13/15*    (2006.01)
*A61F 13/20*    (2006.01)
*A61F 13/42*    (2006.01)

(52) U.S. Cl.
CPC ........... *A61F 13/42* (2013.01); *Y10T 29/4978* (2015.01)

(58) Field of Classification Search
USPC .................................. 604/361, 367, 385.01
See application file for complete search history.

(56) References Cited

U.S. PATENT DOCUMENTS

| 3,675,654 A | 7/1972 | Baker et al. |
| 4,017,820 A * | 4/1977 | Ross ............................... 338/35 |
| 5,570,082 A | 10/1996 | Mahgerefteh et al. |
| 5,838,240 A | 11/1998 | Johnson |
| 5,843,254 A * | 12/1998 | Clark ............................... 156/66 |
| 6,093,869 A * | 7/2000 | Roe et al. ..................... 604/361 |
| 6,284,942 B1 | 9/2001 | Rabin |
| 6,583,722 B2 | 6/2003 | Jeutter et al. |
| 6,677,859 B1 | 1/2004 | Bensen |

(Continued)

FOREIGN PATENT DOCUMENTS

| DE | 3437950 A1 | 4/1985 |
| JP | 11-347058 | 12/1999 |

(Continued)

OTHER PUBLICATIONS

International Search Report and Written Opinion mailed Feb. 29, 2012.

*Primary Examiner* — Michele M Kidwell
(74) *Attorney, Agent, or Firm* — Merchant & Gould P.C.

(57) ABSTRACT

A stacked moisture sensing device and urinary continence monitoring system are disclosed. The stacked moisture sensing device has at least a first media-sensor arrangement adjacent to a second media-sensor arrangement. In one embodiment, each of the media-sensor arrangements has a media layer with a first face, a second face and a side edge that extends between the faces wherein the media layers have differing hydrophilicities. Embedded in each media layer is a moisture sensor which can be a wired type tensor or a wireless RFID type sensor. The stacked moisture sensing device can be used in a variety of applications, such as for use in urinary continence monitoring and for use in shipping containers. In urinary continence monitoring applications, a data collection unit can be provided to acquire data from the sensors, which are located in an absorbent undergarment. Methods for locating the sensors within the absorbent undergarment are also disclosed.

5 Claims, 14 Drawing Sheets

(56) References Cited

U.S. PATENT DOCUMENTS

| | | | |
|---|---|---|---|
| 6,687,524 B1* | 2/2004 | Svejk | 600/391 |
| 6,731,215 B2* | 5/2004 | Harms et al. | 340/605 |
| 6,756,521 B1 | 6/2004 | Breitkopf | |
| 6,774,800 B2 | 8/2004 | Friedman et al. | |
| 6,916,968 B2 | 7/2005 | Shapira et al. | |
| 6,938,482 B2* | 9/2005 | Schultz | 73/335.01 |
| 7,049,969 B2 | 5/2006 | Tamai | |
| 7,141,715 B2 | 11/2006 | Shapira | |
| 7,176,344 B2* | 2/2007 | Gustafson et al. | 604/361 |
| 7,250,547 B1 | 7/2007 | Hofmeister et al. | |
| 7,295,125 B2 | 11/2007 | Gabriel | |
| 7,456,752 B2 | 11/2008 | Oberle | |
| 7,522,061 B2 | 4/2009 | Rondoni et al. | |
| 2002/0145526 A1* | 10/2002 | Friedman et al. | 340/573.5 |
| 2004/0070510 A1 | 4/2004 | Zhang et al. | |
| 2004/0220538 A1* | 11/2004 | Panopoulos | 604/361 |
| 2006/0229578 A1 | 10/2006 | Roe et al. | |
| 2007/0252713 A1 | 11/2007 | Rondoni et al. | |
| 2007/0270774 A1 | 11/2007 | Bergman et al. | |
| 2008/0058680 A1* | 3/2008 | Lee et al. | 600/587 |
| 2008/0150732 A1 | 6/2008 | Bunza et al. | |
| 2008/0161715 A1* | 7/2008 | Stivoric et al. | 600/549 |
| 2008/0297325 A1 | 12/2008 | Torstensson et al. | |
| 2008/0300559 A1* | 12/2008 | Gustafson et al. | 604/361 |
| 2009/0315720 A1 | 12/2009 | Clement et al. | |
| 2010/0030167 A1 | 2/2010 | Thirstrup et al. | |
| 2010/0072271 A1 | 3/2010 | Thorstensson | |
| 2010/0090802 A1 | 4/2010 | Nilsson et al. | |
| 2010/0145294 A1 | 6/2010 | Song et al. | |
| 2010/0300309 A1* | 12/2010 | Schneider | 101/35 |
| 2013/0041334 A1* | 2/2013 | Prioleau et al. | 604/361 |

FOREIGN PATENT DOCUMENTS

| | | |
|---|---|---|
| JP | 2005-602 | 1/2005 |
| JP | 2006-102039 | 4/2006 |
| WO | WO 2005/119195 A1 | 12/1995 |
| WO | WO 2008/130298 A1 | 10/2008 |

* cited by examiner

∧ · AMBULATORY
L · SEATED
— · RECUMBANT

STACKED MOISTURE SENSING DEVICE

TECHNICAL FIELD

The disclosure relates to stacked moisture sensing devices and their uses, such as for use in conjunction with absorbent undergarments and shipping packages.

BACKGROUND

Urinary incontinence is the involuntary loss of urine and affects a significant cross-section of the general population. A number of categories of urinary incontinence exist, such as stress incontinence, urge incontinence, overflow incontinence, and functional incontinence. Additionally, an individual may experience more than one type of incontinence at the same time. Regardless of the cause, urinary incontinence can greatly reduce quality of life by causing embarrassment, stigmatization, isolation, and depression. Individuals may be institutionalized because incontinence has become an overwhelming burden to caregivers. Advances in assessing current and new interventions used for urinary incontinence for a particular individual are desired.

SUMMARY

In order to address incontinence issues in both a chronological and a quantitative manner, it is desirable to reliably monitor the both the timing and the numbers of incontinence episodes throughout a selected time interval, such as during a 24-hour time period of activities of daily living. It is also desirable to assess the duration of exposure of affected areas of skin to moisture from urine throughout the selected evaluation time period, such as during 24-hours of activities of daily living. Through the use of the disclosed stacked moisture sensor monitoring system, it is possible to perform an analysis as to the pattern of incontinence that a given individual is experiencing. Using this information, it is possible to determine the pattern of incontinence, and to then monitor in a data-based manner over time the responses of a given individual to interventions selected for that individual's incontinence, for example, exercises, pharmaceuticals, medical devices and/or surgical procedures. Furthermore, the outcome of the selected interventions can be quantified through further use of the urinary incontinence monitoring system by comparing pre- and post-intervention evaluation period data. By proceeding in this manner, response to interventions can be understood both before and after the selected interventions for that individual during selected monitoring period during activities of daily living. Depending on the outcomes as measured by data collected with the stacked moisture sensor device, current interventions can either be continued as is or additional or different interventions can be selected.

A stacked moisture sensing device having at least a first and a second media-sensor arrangement is disclosed. In one embodiment, each of the media-sensor arrangements has a media layer with a first face, a second face and a side edge that extends between the first and second faces. Each media layer also has a hydrophilicity that is different from a hydrophilicity of the other media layers in the stack. Embedded in each media layer is a moisture sensor which can be a wired type moisture sensor or a wireless RFID type sensor. The stacked moisture sensing device can be used in a variety of applications, such as for use in urinary continence monitoring and for use in shipping containers. The stacked moisture sensing device can be used in a method of monitoring continence of a human being by providing the moisture sensing device and securing the device to an absorbent undergarment.

A urinary continence monitoring system is also disclosed using the above described stacked moisture sensing devices in conjunction with an absorbent undergarment and data collection unit. The absorbent undergarment can be provided with an indicia pattern to indicate the locations where the stacked moisture sensing devices should be located. Multiple indicia patterns on the same undergarment are disclosed as well.

Also disclosed is a method for locating moisture sensing devices on an absorbent undergarment. The method includes providing a template and an absorbent undergarment, and then transferring an indicia pattern from the template to the absorbent undergarment. Subsequently, an additional step of placing the moisture sensing devices on the absorbent undergarment in locations corresponding to the transferred indicia pattern is performed. Also, it is also possible to place the template over an absorbent undergarment being worn by a user and marking the desired locations for the moisture sensors onto the template to form the indicia pattern.

BRIEF DESCRIPTION OF THE DRAWINGS

FIG. 31b is a cross-sectional view of the wired stacked moisture sensing device shown in FIG. 31a.

DETAILED DESCRIPTION

Figure 2:
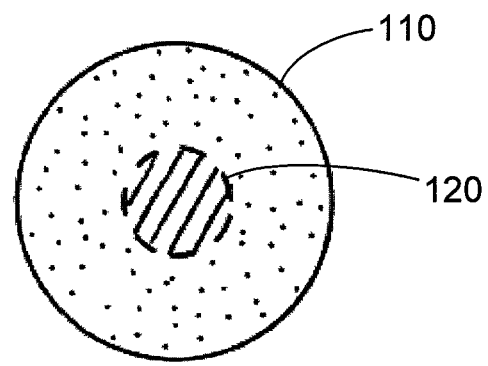
FIG. 2 is a top view of the stacked moisture sensing device shown in FIG. 1.
Figure 3:
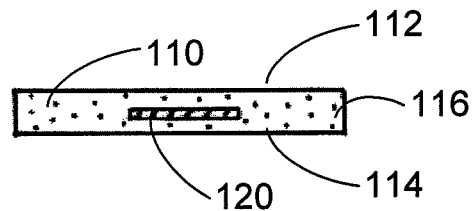
FIG. 3 is a cross-sectional view of a media-sensor arrangement of the stacked moisture sensing device shown in FIG. 1.

This disclosure relates to a stacked moisture sensing device 100 and applications suitable for use with the disclosed device, such as for a urinary continence monitoring system. The stacked moisture sensing device is for monitoring the characteristics of moisture exposure to a person' skin or to the contents of a package. One example of such a stacked moisture sensing device is shown on FIGS. 1-3.

Figure 10:
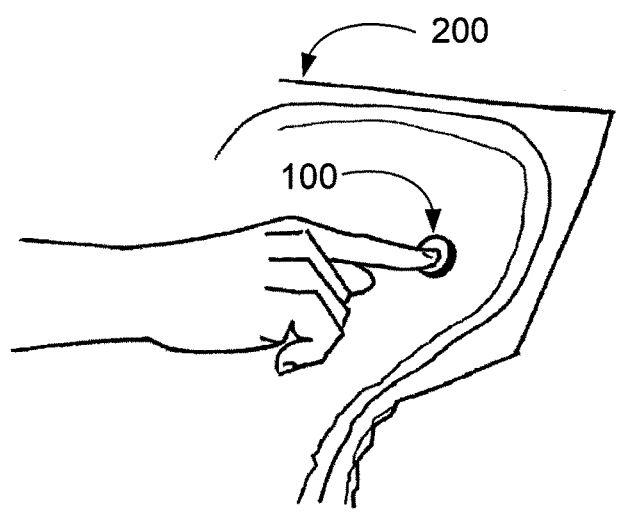
FIG. 10 is a view of a practitioner installing the stacked moisture sensing device shown in FIG. 8 onto an absorbent undergarment.
Figure 11:
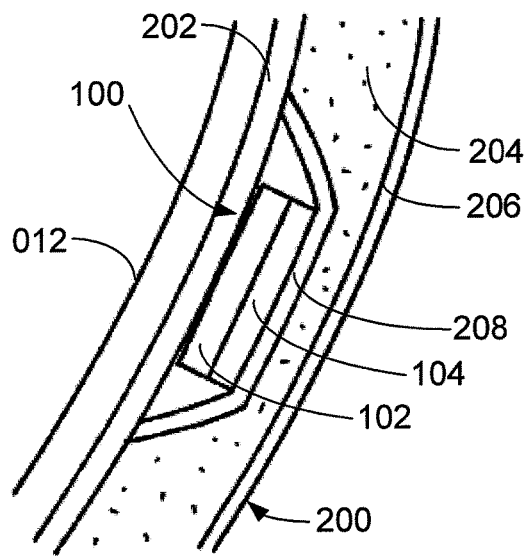
FIG. 11 is a cross-sectional view of an absorbent undergarment and a stacked moisture sensing device in a first arrangement.
Figure 12:
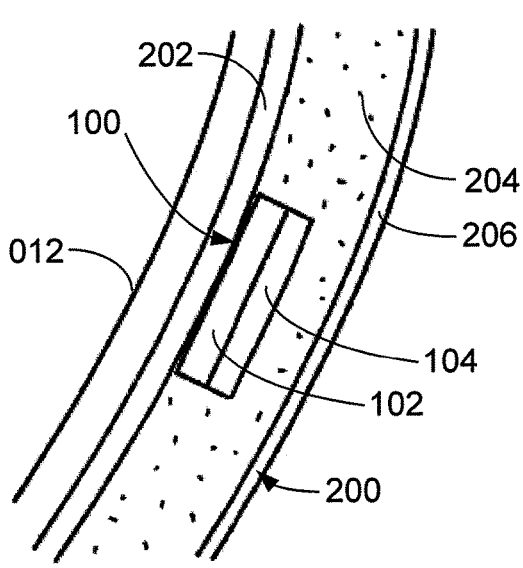
FIG. 12 is a cross-sectional view of an absorbent undergarment and a stacked moisture sensing device in a second arrangement.

In one exemplary embodiment, the stacked moisture sensing device 100 has a plurality of media-sensor arrangements that are stacked upon each other. In the particular embodiment shown in FIG. 1, the stacked moisture sensing device 100 has a first media-sensor arrangement 102, a second media-sensor arrangement 104, and a third media-sensor arrangement 106. Each media-sensor arrangement is constructed to simultaneously control the flow of moisture and to monitor the level of moisture within the arrangement. One skilled in the art will readily appreciate that any number of media-sensor arrangements may be stacked upon each other to achieve this purpose. For example, FIGS. 10-12 show a stacked moisture sensing device 100 that includes only two stacked media-sensor arrangements wherein the first media-sensor arrangement 102 is adjacent to a person's skin 012. It is also possible that more than three media-sensor arrangements may be stacked together.

Each of the media-sensor arrangements is shown as comprising a media layer 110 and a sensor 120, discussed later, embedded within each media layer 110. As shown, each media layer 110 shown has a first face 112, a second face 114 opposite the first face 112, and a side edge 116 extending between the first and second faces. As shown in the drawings, each media layer 110 is in the general shape of a disk having a diameter of about 3 centimeters and a thickness of about 0.5 centimeters. However, one skilled in the art will readily appreciate that other sizes and shapes are possible without departing from the disclosed concepts herein. To form the stacked media sensing device 110, the sensor-media arrangements 102, 104, 106 are stacked upon each other such that at least one of the media layer faces 112, 114 of each sensor-media arrangement 102, 104, 106 is in direct contact with another media layer face 112, 114 of the adjacent sensor-media arrangement 102, 104, 106.

Each media layer 110 also has a given hydrophilicity. As used herein, the term "hydrophilicity" means the degree to which the media has an affinity for absorbing water. Thus, a media layer having a relatively high hydrophilicity will rapidly absorb moisture and would also be termed as being hydrophilic. In contrast, a media layer having a low hydrophilicity will absorb very little or no water and would also be termed as being relatively hydrophobic. In the exemplary embodiments shown in FIGS. 1-12, the media layer 110 of each media sensor-arrangement 102, 104, 106 has a hydrophilicity that is different from the hydrophilicity of every other media layer 110. By providing layers having differing hydrophilicities, the flow and storage of moisture passing into or through the stacked moisture sensing device can be controlled, as desired, for any particular application.

As stated above, materials that may be used for media layer 110 having a relatively low hydrophilicity would allow liquids (e.g., urine) to readily pass through the media layer 110. Examples of such materials are polymeric materials, such as polyester, polypropylene, or polyethylene fibers, or a combination thereof. These materials may be woven or nonwoven. In the embodiment shown in FIGS. 10-12, the media layer 110 of media-sensor arrangement 102 is made from a liquid permeable hydrophobic material (low hydrophilicity) to isolate a user's skin 012 from liquids contained in the media layer 110 of media-sensor arrangement 104.

Figure 1:
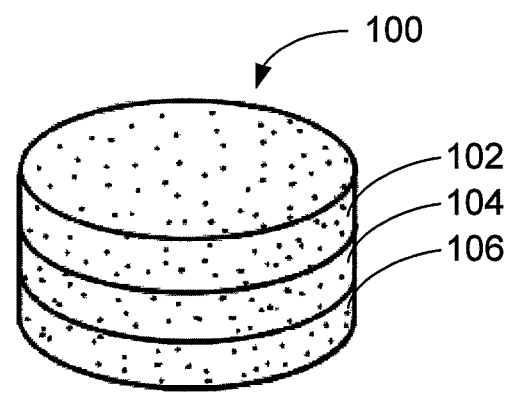
FIG. 1 is a perspective view of a first embodiment of a stacked moisture sensing device.
Figure 4:
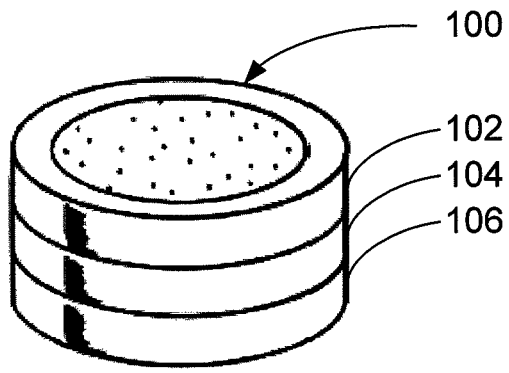
FIG. 4 is a perspective view of the stacked moisture sensing device shown in FIG. 1 having a first embodiment of an edge covering.
Figure 5:
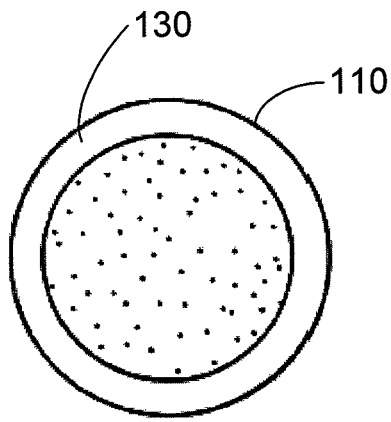
FIG. 5 is a top view of the stacked moisture sensing device shown in FIG. 4.
Figure 6:
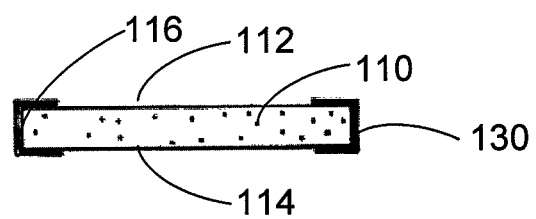
FIG. 6 is a side view of a media layer and a moisture sensor of the stacked moisture sensing device shown in FIG. 4.
Figure 7:
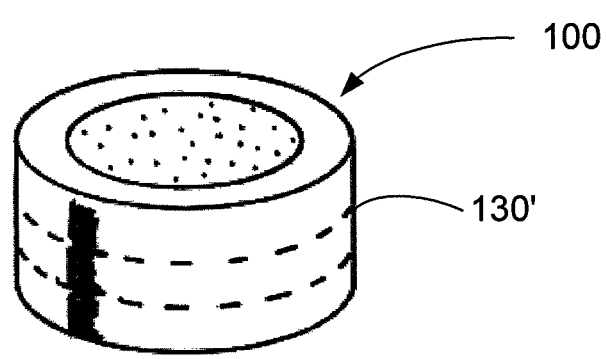
FIG. 7 is a perspective view of the stacked moisture sensing device shown in FIG. 1 having a second embodiment of an edge covering.

Many materials may also be used for media layer 110 having a relatively high hydrophilicity that would allow liquids (e.g., urine) to be absorbed by the media layer 110. For example, suitable materials include fibrous nonwoven materials, fibrous air-laid materials, fibrous wet-laid web materials, fibrous spun-bond materials, and combinations of fibrous materials having absorbent gelling materials dispersed upon or within the fibrous structure. Absorbent materials may contain naturally absorbent components such as cellulose fibers (e.g. cotton, wood pulp, etc.) or may be synthetic (e.g. super absorbent polymers and foams), or may include a combination of natural and synthetic materials. In the embodiment shown in FIGS. 10-12, the media layer 110 of media-sensor arrangement 104 is made from a hydrophilic material (high hydrophilicity) to absorb moisture that has passed through the media layer 110 of media-sensor 102 and/or to absorb liquid from the absorbent undergarment 200 itself. In the embodiments of FIGS. 1, 4, and 7, media layer 110 of media-sensor 102 can have low hydrophilicity, media layer 110 of media-sensor 104 can have an intermediate level of hydrophilicity, and media layer 110 of media-sensor 106 can have a high level of hydrophilicity. For example, media layer 110 of media-sensor 102 can be made of 100% polyester or microfiber material, media layer 110 of media-sensor 104 can be made of a blend of cotton and synthetic materials while media layer 110 of media-sensor 106 can have 100% natural fibers, including cotton fibers and wood pulp fibers, or be comprised of super absorbent polymers. For the intermediate layer, or any layer for that matter, the hydrophilicity can be tightly controlled by blending materials, such as cotton and polyester fibers, together in differing ratios and/or configurations. One skilled in the art will appreciate that the number and order of the media layers, and their respective hydrophilicities, may be arranged in any manner to meet the design criteria for any given application. One skilled in the art will also readily appreciate that the materials for the media layers may be chosen to match the materials used in a particular absorbent undergarment.

As stated above, each media sensor arrangement includes a sensor 120. Sensor 120 is for detecting the presence of moisture or of voiding within each media layer 110. Many types of sensors are suitable for this purpose, such as pressure sensors, wetness sensors, pH sensors, humidity sensors, deformation sensors, or any other sensor capable of converting electrical or chemical conditions representative of voiding information into electrical signals. The conversion into electrical signals may be based electrical impedance, resistance, or capacitance depending upon the application and sensor type. One example of a moisture detecting sensor is described in US Patent Application Publication 2009/0315720 which discloses a radio frequency identification (RFID) tag and moisture sensor that, once exposed to moisture, completes a battery and transmits a signal to an RFID reader. U.S. 2009/0315720 is hereby incorporated by reference in its entirety. Other RFID based moisture detection systems are disclosed in U.S. Patent Application Publication 2010/0090802 and WO 2005/119195, both of which are also incorporated by reference in their entirety into this application.

Figure 31:
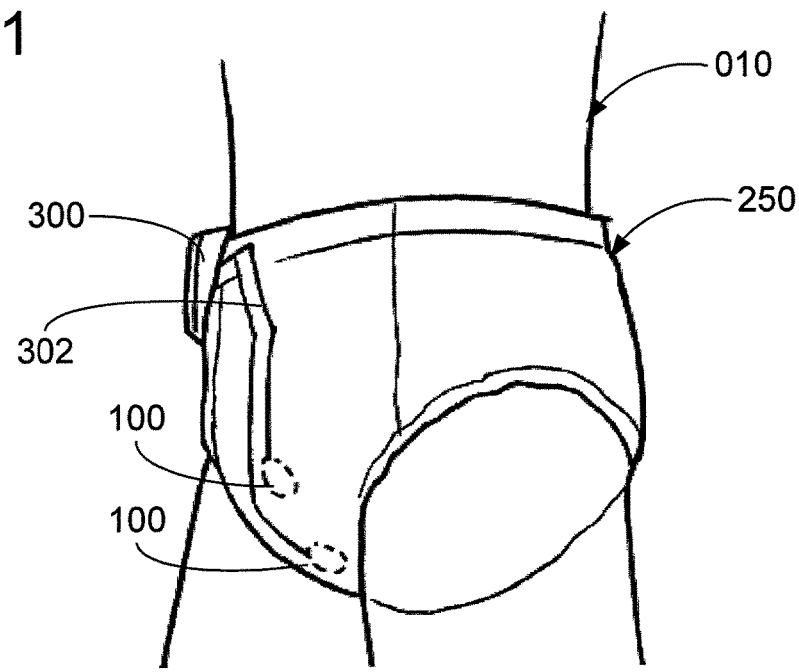
FIG. 31 is a perspective view of an absorbent undergarment and a wired data collection unit.
Figure 31A:
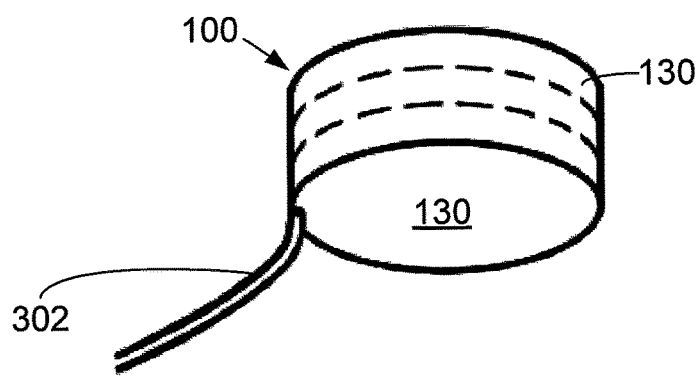
FIG. 31a is a perspective view of a wired stacked moisture sensing device used in the absorbent undergarment shown in FIG. 31.
Figure 31B:
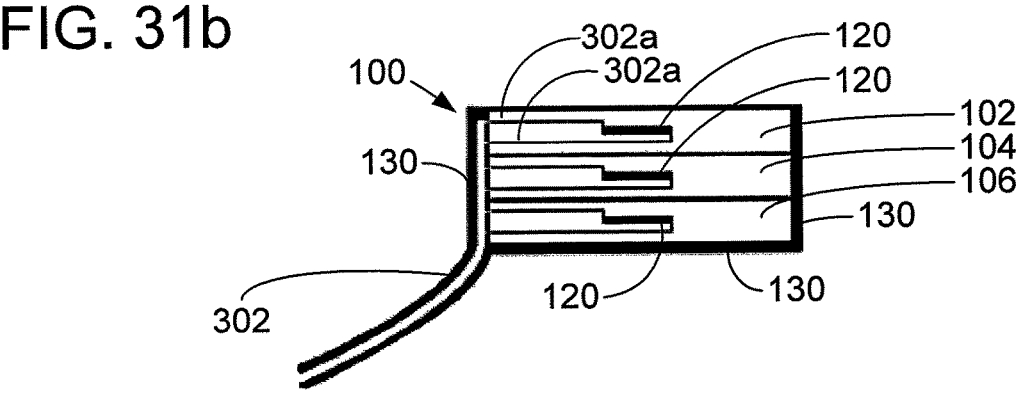
Figure 32:
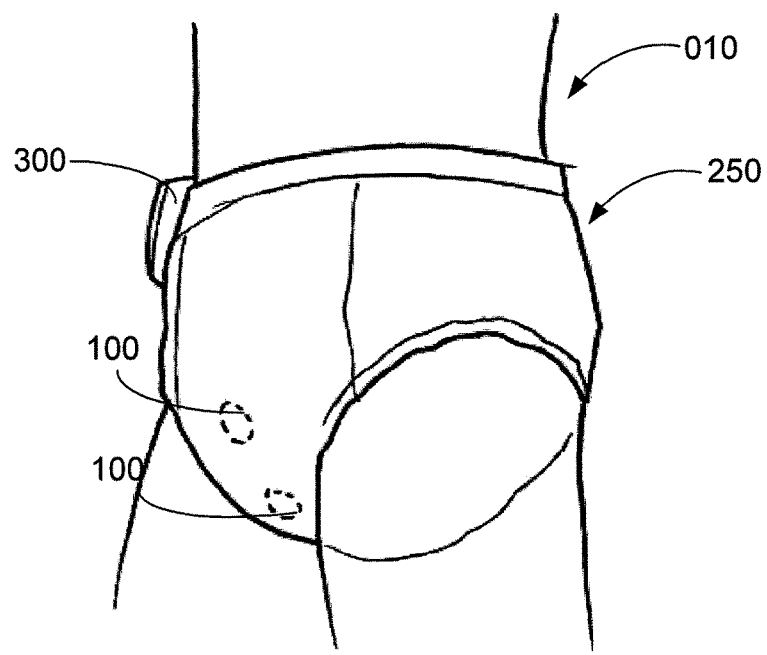
FIG. 32 is a perspective view of an absorbent undergarment and a wireless data collection unit.

The sensors can also be wired to a data collection unit 300, or communicate wirelessly with the data collection unit. By use of the term "wired", it is meant to include any sensor that utilize wire(s) for communication and/or power. Where wireless communication is desired, RFID units can be used which may be passive, semi-passive, or active. Active and semi-passive RFID utilize internal batteries to power their circuits. An active RFID unit also uses its battery to transmit radio waves to the data collection unit 300, whereas a semi-passive unit relies on the data collection unit 300 to supply its power for transmitting signals. Passive RFID tags rely entirely on the data collection unit 300 as their power source. In the example shown in FIG. 32, each sensor 120 is an RFID type sensor wherein data from the sensor 120 is transmitted to a data collection unit 300 via wireless transmission. Where each sensor 120 requires wired data communication and/or power, the data collection unit 300 can provide a wired connection 302 to each sensor 120, as shown in FIGS. 31-31b. As shown in FIGS. 31a and 31b, wired connection 302 enters moisture barrier 130, preferably in a water tight manner, and connects to each individual sensor 120 via leads 302a and 302b. Wired connection 302 can be routed to the data collection unit 300 through the undergarment 200 material, or can be routed along the surface of the undergarment 200.

Figure 8:
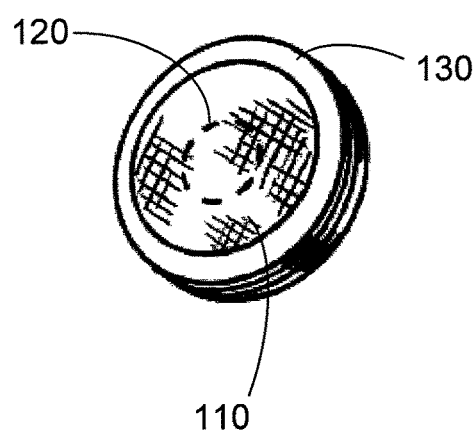
FIG. 8 is a front perspective view of the stacked moisture sensing device shown in FIG. 1 having a third embodiment of an edge covering.
Figure 9:
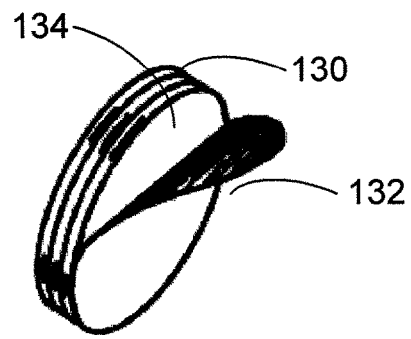
FIG. 9 is a rear perspective view of the stacked moisture sensing device shown in FIG. 8.

An edge covering 130 can also be provided extends along the side edge 116 of each media layer 110. Edge covering 130 can serve the function of preventing moisture from entering the side edges 116 of the media layers 110, protecting the side edges 116, and/or providing a containment of the media layers 110. Many embodiments of an edge covering 130 are suitable for these purposes. In the exemplary embodiment shown in FIGS. 4-6, an edge covering 130 is provided that individually surrounds each media layer 110, and also partially covers the first and second faces 112, 114 of each media layer 110. One skilled in the art will appreciate that edge covering 130 could also entirely cover the first and second faces 112, 114 of each media layer 110 as well. Furthermore, that portion which does cover the first and second faces 112, 114 may be provided with an adhesive 134 such that the layers may be stacked and adhered to one another. Instead of providing an individual edge covering 130 over each media layer 110, a unitary edge covering 130 can also be provided, as shown in FIGS. 7, 31a, and 31b. Once example of an edge covering 130 is shown in FIGS. 8-10 wherein the edge covering 130 extends beyond the side edges 110 of the media layers 102 and 106. In this particular embodiment, edge covering 130 covers the entire second face 114 of media layer 106, and is provided with an adhesive coating 134 for attaching the stacked moisture sensing device 100 to an absorbent undergarment, a package, or any other surface where it is desirable to monitor moisture conditions. A backing layer 132 can also be provided to protect the adhesive coating 134 before use. Depending upon the application, edge covering 130 may be water impermeable to serve as a moisture barrier, or may be water permeable to allow liquids to enter the media layers through their side edges. Furthermore, edge covering 130 may be made of a flexible material that will accommodate the expansion of any of the media layers 110 when exposed to moisture.

Figure 13:
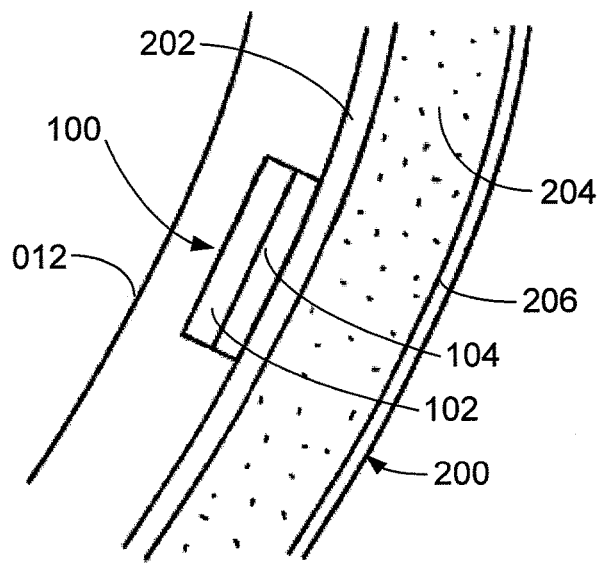
FIG. 13 is a cross-sectional view of an absorbent undergarment and a stacked moisture sensing device in a third arrangement.

One application for the disclosed stacked moisture sensing device 100 is in conjunction with an absorbent undergarment 200. An absorbent undergarment is any wearable garment that is designed to absorb moisture. Non-limiting examples of absorbent undergarments include disposable and reusable diapers, PULL-UPS®, underwear, urine guards/shields, and sheets designed to be placed under an individual in a reclined position. A well known manufacturer of these types of undergarments is Kimberly Clark, the manufacturer of the DEPENDS® brand of incontinence products. In such an application, data collected from the sensor 120 of each installed sensing device 100 can be analyzed to identify and evaluate a variety of incontinence issues. In the embodiments shown in FIGS. 10-13, a stacked moisture sensing device 100 is shown attached to an absorbent undergarment 200 having a pass through layer 202, an absorbent layer 204, and a backing layer 206. The stacked moisture sensing device 100 may be attached to the absorbent undergarment in a variety of ways. For example, as shown in FIGS. 10 and 13, the stacked moisture sensing device 100 may be attached directly on top of the pass through layer 202 such that the first media-sensor arrangement 102 will be adjacent to the user's skin 012. Alternatively, and as shown in FIGS. 11 and 12, the stacked moisture sensing device 100 may be inserted beneath the pass through layer 202 of the absorbent undergarment. With specific respect to FIG. 11, the stacked moisture sensing device 100 is placed within a pocket of the absorbent undergarment 200 defined by the pass through layer 202 and an additional pass through layer 208, which may be moisture permeable or impermeable. The pocket serves the function of isolating the stacked moisture sensing device 100 from direct contact with the absorbent layer 204 of the absorbent undergarment 200. With specific reference to FIG. 12, the stacked moisture sensing device 100 may be placed within the absorbent layer 204. It is noted that the moisture sensing device 100, or a plurality of devices 100, may be installed during the manufacturing process of the absorbent undergarment 200 or after the manufacturing process. Although the sensing device(s) 100 may be installed in an undergarment 200 specifically designed to receive the sensors, a benefit of the disclosed device 100 is that it may be attached to virtually any absorbent undergarment 200 regardless of its manufacture.

Where stacked moisture sensing device 100 is constructed using a moisture impermeable edge covering 130 in conjunction with an absorbent undergarment 200, moisture flow can be controlled and monitored by tracking the saturation level of the various media layers. For example, where the media layers have increasing hydrophilicity from layer 102 to layer 106, moisture initially exposed to the media 110 of layer 102 will eventually be absorbed or wicked into the media 110 of layer 104. In turn, at least some of the moisture present in the media 110 of layer 104 will then be absorbed into the media 110 of layer 106. This migration of moisture will continue to occur until the media 110 of layer 106 has reached full saturation and is then no longer able to absorb further moisture. At that point, the media 110 of layer 104 will then become increasingly saturated until it reaches its saturation point and is no longer able to absorb additional moisture from the media 110 of layer 102. Subsequently, the media 110 of layer 102 will remain in a fully wet state. As this process occurs, the respective moisture sensors in the media layers will increasingly show their status as being wet in a binary sensor application, or as having a higher and higher relative humidity level with an analog humidity sensor. By collecting the moisture sensor data, including the frequency of events and the time over which saturation at each level occurs, the nature of moisture exposure may be analyzed and understood. This determination is especially enhanced when multiple devices 100 are utilized within the same undergarment 200. Additionally, a reference sensor(s) that is not embedded in media may also be utilized to monitor a variety of conditions such as the number of voiding episodes or to signify whether a certain portion of skin is exposed to moisture.

Figure 34:
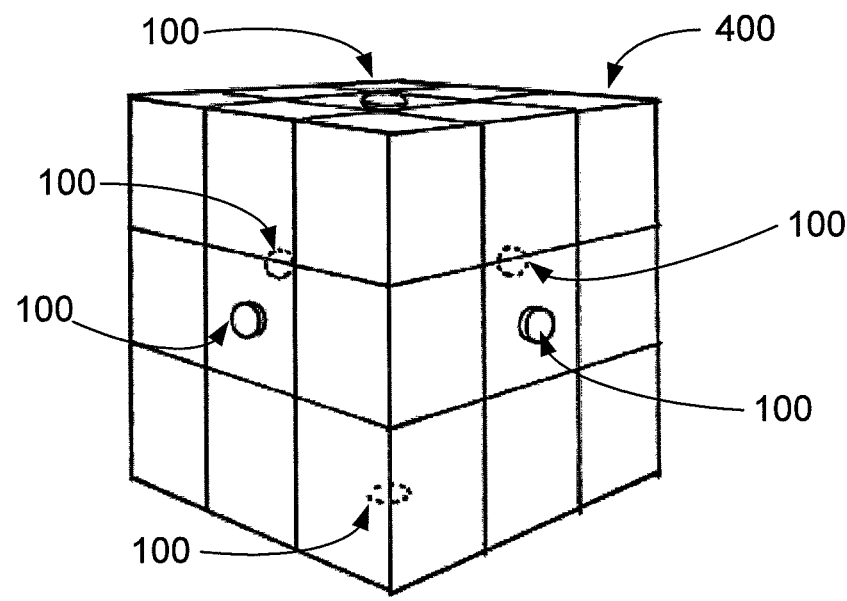
FIG. 34 is a perspective view of a shipping package with stacked moisture sensors installed.
Figure 35:
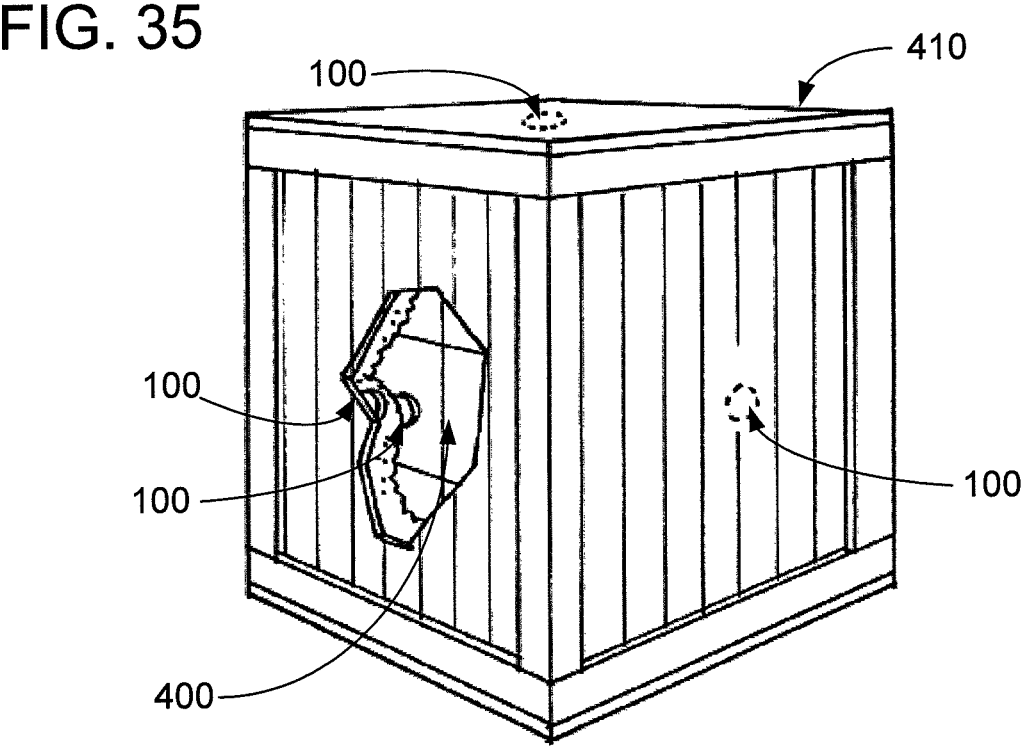
FIG. 35 is a perspective view of a shipping container with stacked moisture sensors installed.
Figure 36:
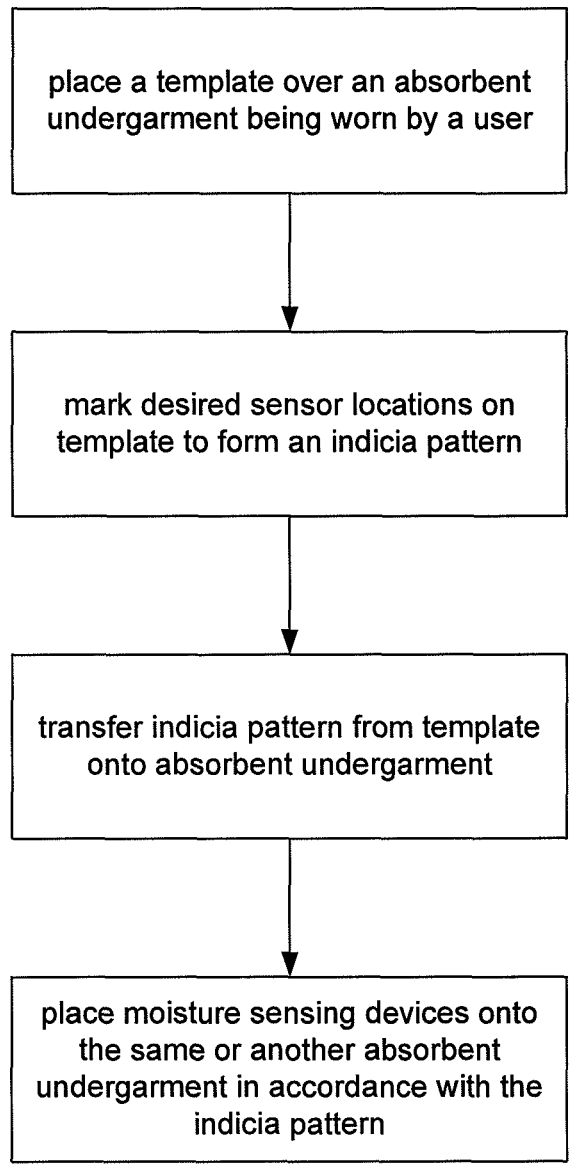
FIG. 36 is a flow chart showing steps for a method of locating moisture sensing devices on a disposable undergarment.

Another application for the disclosed stacked moisture sensing device 100 is in conjunction with the shipping of packages and/or containers. In such an application, data collected from the sensor 120 of each installed device 100 can be analyzed to verify that proper moisture and humidity levels have been maintained during shipment. In the embodiments shown in FIGS. 34-35, a plurality of stacked moisture sensing devices 100 are shown attached at various locations on a package 400 and a container 410 holding the package 400. With such an embodiment it is possible to provide an indication of moisture levels over time where the sensors are in data communication with a data collection unit.

Figure 14:
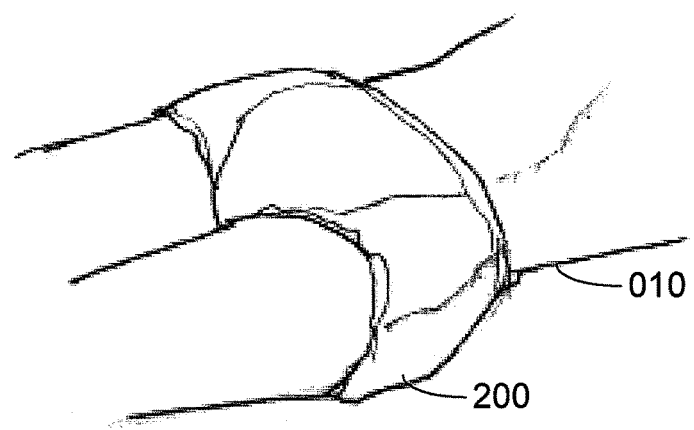
FIG. 14 is a partial perspective view of a user wearing an absorbent undergarment in a reclined position.
Figure 15:
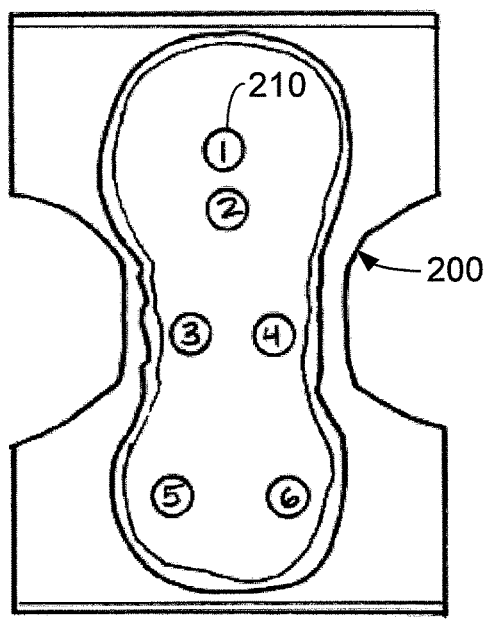
FIG. 15 is a top view of the absorbent undergarment shown in FIG. 14 showing a first example of a location pattern for the placement of moisture sensors.
Figure 16:
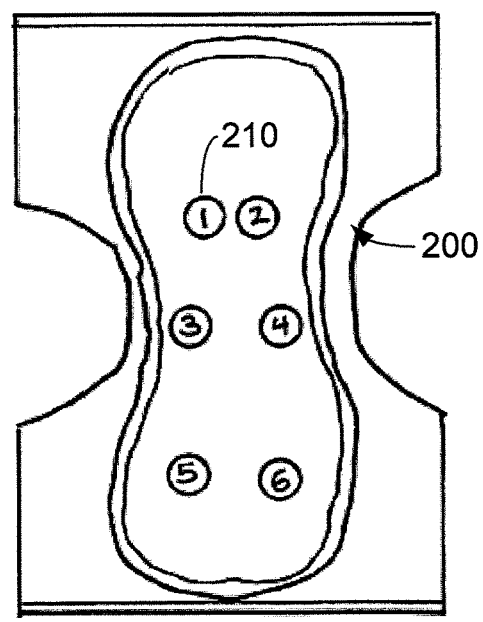
FIG. 16 is a top view of the absorbent undergarment shown in FIG. 14 showing a second example of a location pattern for the placement of moisture sensors.
Figure 17:
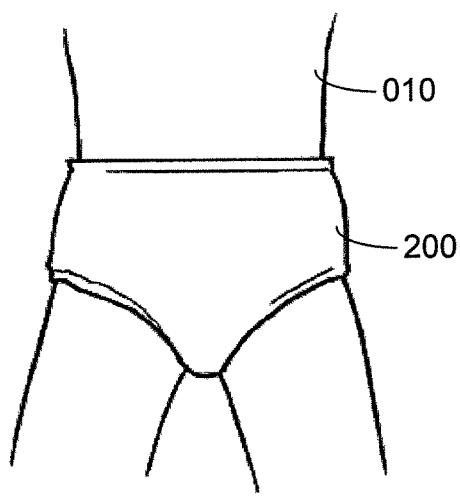
FIG. 17 is a partial perspective view of a user wearing an absorbent undergarment in an ambulatory position.
Figure 18:
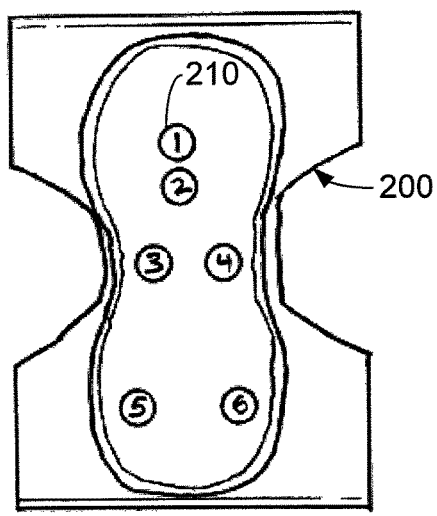
FIG. 18 is a top view of the absorbent undergarment shown in FIG. 17 showing a first example of a location pattern for the placement of moisture sensors.
Figure 19:
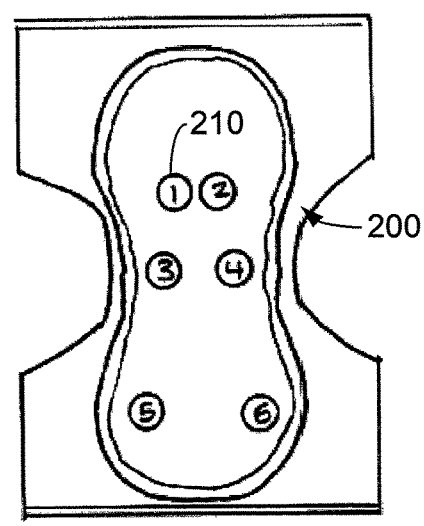
FIG. 19 is a top view of the absorbent undergarment shown in FIG. 17 showing a second example of a location pattern for the placement of moisture sensors.
Figure 20:
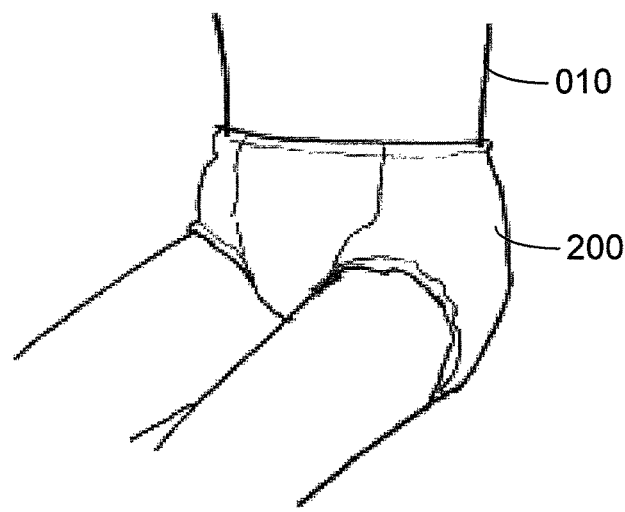
FIG. 20 is a partial perspective view of a user wearing an absorbent undergarment in an seated position.
Figure 21:
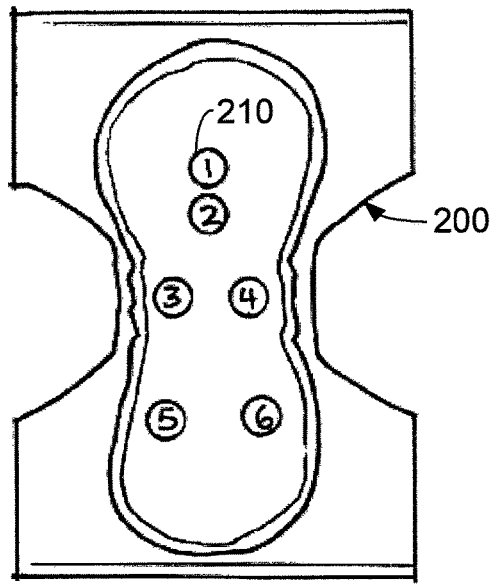
FIG. 21 is a top view of the absorbent undergarment shown in FIG. 20 showing a first example of a location pattern for the placement of moisture sensors.
Figure 22:
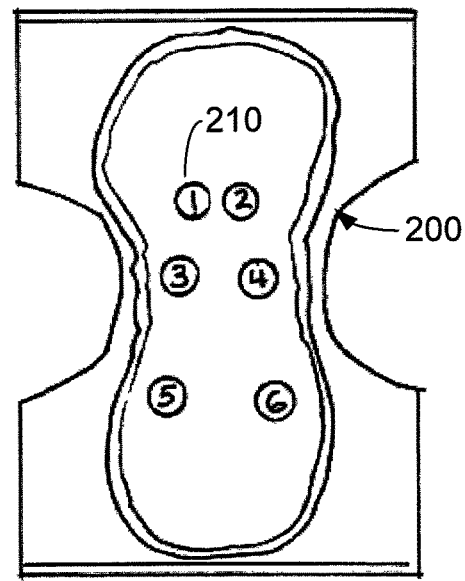
FIG. 22 is a top view of the absorbent undergarment shown in FIG. 20 showing a second example of a location pattern for the placement of moisture sensors.

As stated above, a plurality of stacked moisture sensing devices 110 can be placed within a single absorbent undergarment 200. One way to determine the number and placement of the stacked moisture sensing devices 110 within an absorbent undergarment is to define a pattern based upon factors defining where moisture is likely to migrate within the absorbent undergarment 200 most heavily. Examples of such factors are the gender of the user 010 and the anticipated primary position of the user 010. In the examples shown in FIGS. 14-22, a sensor location pattern 210 is shown (labeled 1-6) that is based on both the gender of the user 010 and the anticipated primary position of the user 010. FIG. 14 shows a user 010 wearing an absorbent undergarment 200 in a reclining position. FIG. 15 shows one potential sensor location pattern 210 that could be used for a male user 010 in a primarily reclined position while FIG. 16 shows another potential sensor location pattern 210 that could be used for a female user 010. In another example, FIG. 17 shows a user 010 wearing an absorbent undergarment 200 in an ambulatory position. FIG. 18 shows one potential sensor location pattern 210 that could be used for a male user 010 in a primarily ambulatory position while FIG. 19 shows another potential sensor location pattern 210 that could be used for a female user 010. In yet another example, FIG. 20 shows a user 010 wearing an absorbent undergarment 200 in a seated position. FIG. 21 shows one potential sensor location pattern 210 that could be used for a male user 010 in a primarily seated position while FIG. 22 shows another potential sensor location pattern 210 that could be used for a female user 010.

Figure 23:
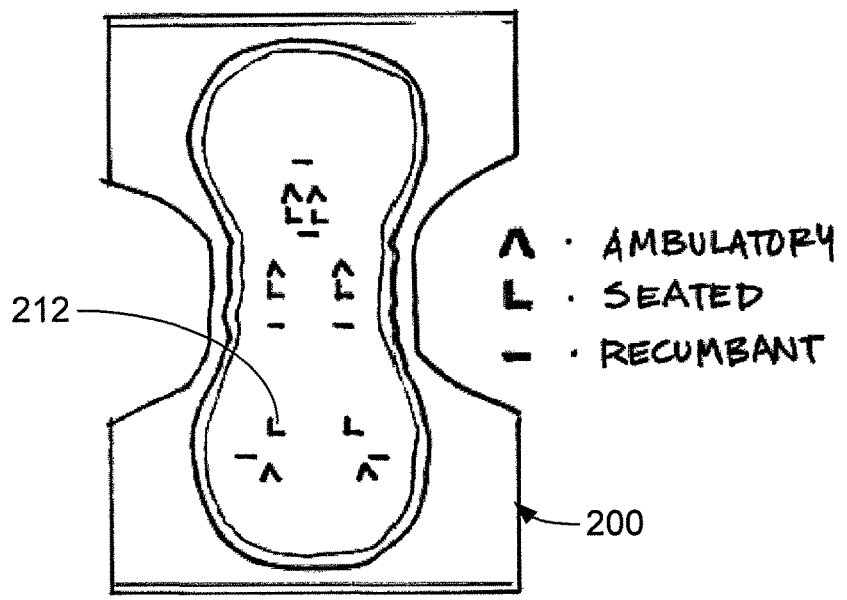
FIG. 23 is a top view of an absorbent undergarment having multiple indicia patterns.

It is also noted that the absorbent undergarment 200 can be provided with an indicia pattern 212 to help identify where the stacked moisture sensing devices 100 are to be located on the absorbent undergarment 200. Many types of indicia are suitable for this purpose. One example of such an indicia pattern is shown in FIG. 23 where three separate patterns are identified through the use of different shapes. However, one skilled in the art will readily understand that many other types of indicia are possible, such as by using colors, numbers and/or text to differentiate the patterns. As shown, the indicia pattern provides an indication for where sensors could be located based on three different anticipated user 010 positions. The indicia pattern can be pre-printed onto the absorbent undergarment 200 at the time of manufacture or can be added at a later time.

Figure 24:
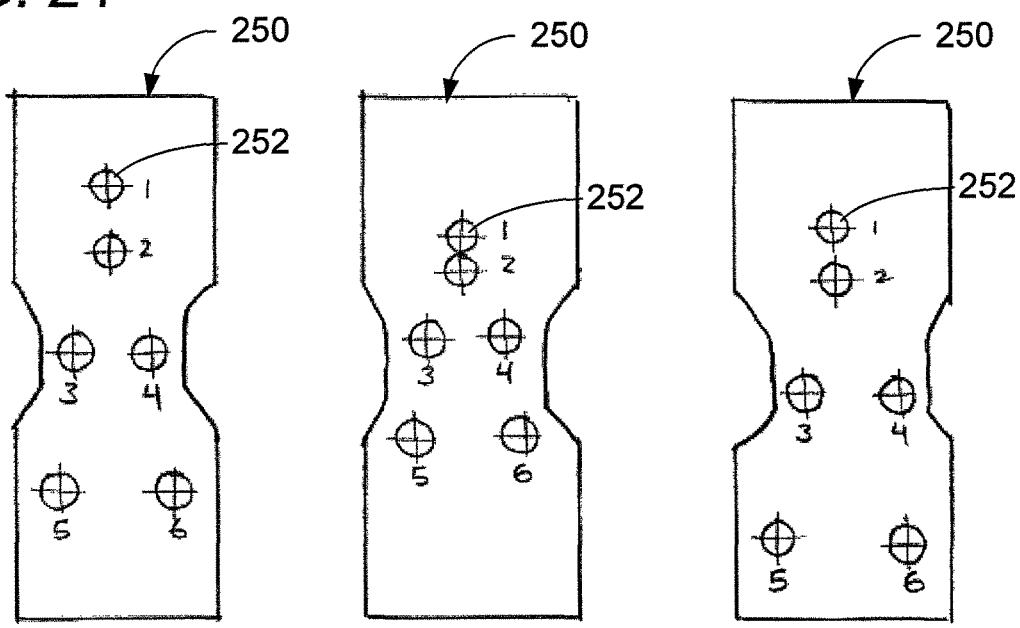
FIG. 24 is a top view of three templates each having a single indicia pattern.
Figure 25:
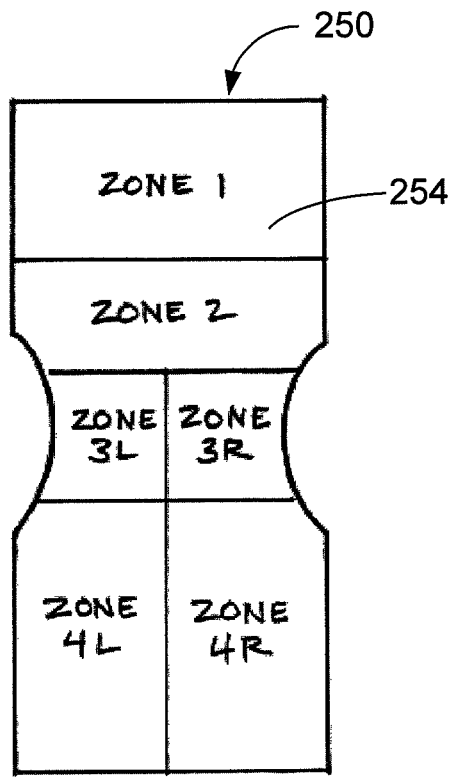
FIG. 25 is a top view of a template having a zone pattern.
Figure 26:
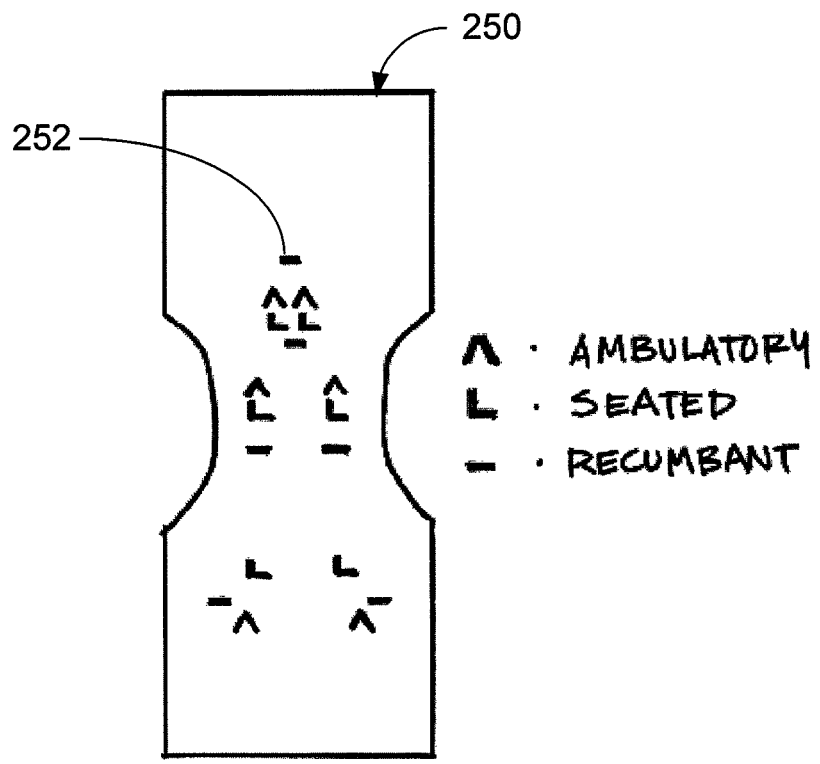
FIG. 26 is a tope view of a template having multiple indicia patterns.

One such way that the absorbent undergarment 200 may be marked with an indicia pattern 212 after the time of manufacture is through the use of a template 250 having an indicia pattern 252, as shown in FIGS. 24-30. One benefit of using such a template 250 is that an easy record can be made of where the sensing devices 100 are located on the absorbent undergarments 200. Another benefit of using a template 250 to identify the sensor locations is that it is not necessary to have a specialized absorbent undergarment 200. Many examples of indicia patterns 252 for the template 250 exist. For example, FIG. 24 shows three templates 250 with each having a separate indicia pattern 252 while FIG. 26 shows an indicia pattern similar to that shown on the absorbent undergarment 200 in FIG. 23. Another example is shown in FIG. 25 where separate zones are defined instead of specific locations for each sensor. When using a template 250, the indicia pattern 252 is replicated on the absorbent undergarment 200 to define the moisture sensing device 100 locations. Transferring the indicia pattern 252 can be accomplished in a variety of ways. For example, the template can be overlaid onto the absorbent undergarment and the template can be punctured at each sensor location (labeled 1-6)

and marked with a pen. Alternatively, the template can have holes such that puncturing the template is not required.

Figure 27:
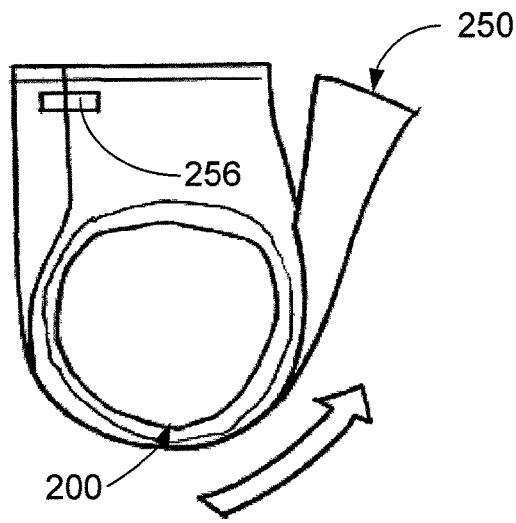
FIG. 27 is a side view of an absorbent undergarment with a template partially installed.
Figure 28:
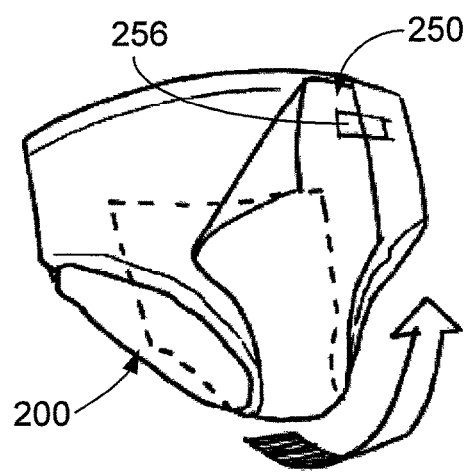
FIG. 28 is a front perspective view of the absorbent undergarment and template shown in FIG. 26.
Figure 29:
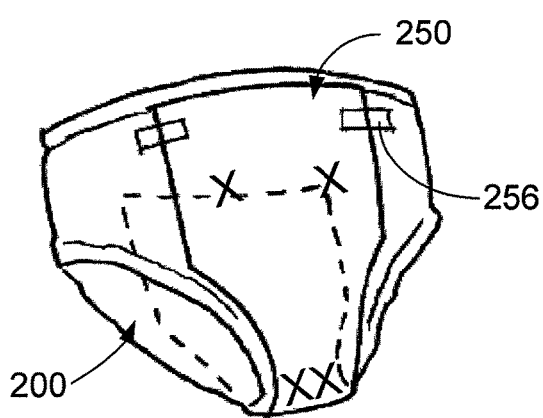
FIG. 29 is a front perspective view of the absorbent undergarment and template shown in FIG. 26 with the template completely installed.
Figure 30:
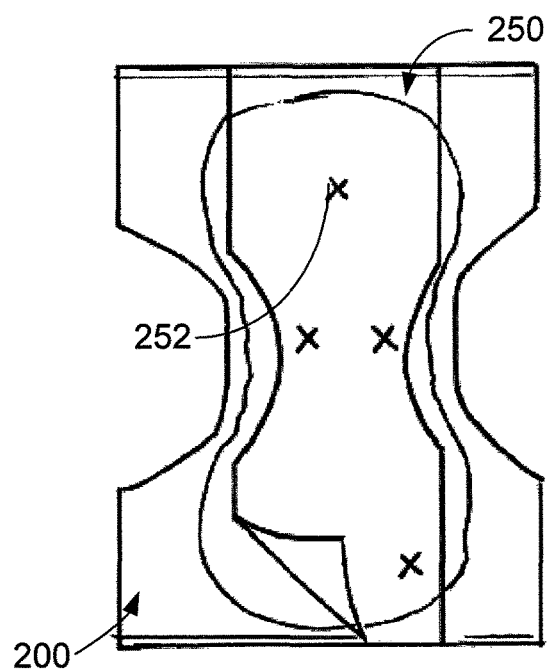
FIG. 30 is a top view of the template and absorbent undergarment shown in FIG. 26 with the template overlaying the absorbent undergarment.

The indicia pattern 252 on the template 250 can be either pre-printed or can be custom marked. FIGS. 27-30 and 36 show a process for custom marking a blank template. In a first step, the template 250 is placed over an absorbent undergarment 200 that is being worn by a user. This step is shown in FIGS. 27-29, where the template 200 is temporarily attached to the undergarment with fasteners 256. Once attached, the desired locations for the sensing devices 100 can be marked to form the indicia pattern 252, as shown in FIG. 29. Once the indicia pattern 252 is marked, the template can be removed and overlaid onto the absorbent undergarment 200, as described above and shown in FIG. 30.

Figure 33:
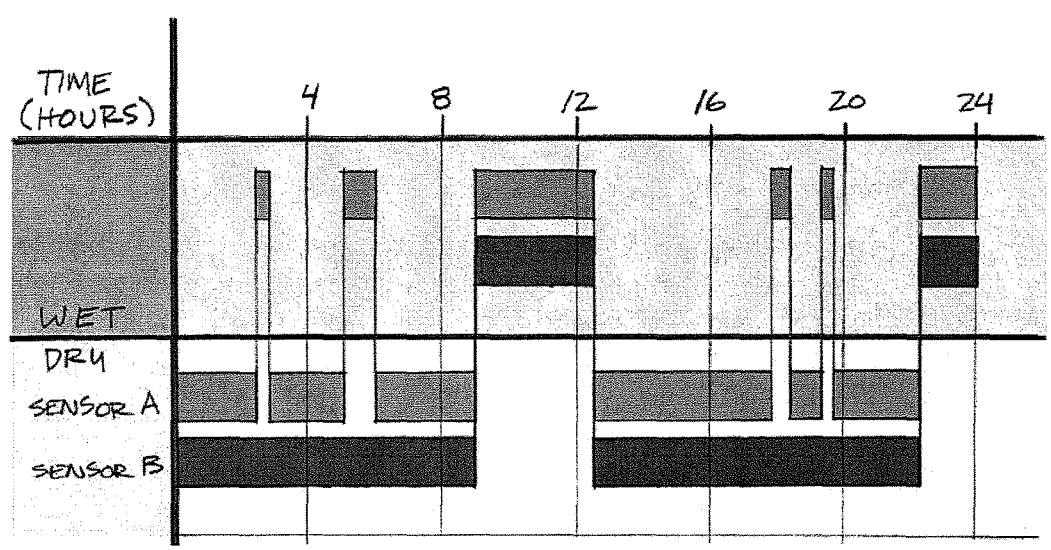
FIG. 33 is a graph showing exemplary output received to the data collection unit shown in FIGS. 31 and 32.

When using the above described system, is possible to obtain a variety of data regarding the exposure of the sensors 120 and media layers 100 to moisture. An example of such data is represented in graphical form in FIG. 33. In the configuration represented by FIG. 33, the first sensor-media arrangement 102 (Sensor A) is exposed to moisture initially which is then absorbed by the second sensor-media arrangement 104 (Sensor B). Over time, the sensor 120 (Sensor A) in the first sensor-media arrangement cycles through wet and dry periods until the media layer 100 of the second sensor-media arrangement 104 becomes sufficiently saturated to trigger the embedded moisture sensor 120 (Sensor B). As shown on the graph in FIG. 33, this occurs at approximately 9 hours. At shortly after 12 hours on the graph, the moisture sensing device 100 is replaced with a new moisture sensing device 100 and the process is started over again. Another example of how the output data can be shown is provided in Table 4B below.

The following tables, Table 1 to Table 4B show an example of how user 010 information can be organized with respect to the moisture data collected from the data collection unit 300. Additionally, the individual tables outline a method by which urinary continence can be monitored before and after an intervention to evaluate whether an intervention has caused a change in the urinary incontinence pattern.

As shown below, Table 1 provides information regarding the user 010 and the period of time over which the data collection unit was activated.

TABLE 1

Identification Information for Moisture Monitor System

| Subject | Date and Time |
|---|---|
| Name: | Start date: |
| Birth date: | Start time: |
| Gender: | Stop date: |
| Height: | Stop time: |
| Weight: | Duration: |

Female or male: surgical history

| Date | Procedure | Date | Procedure |
|---|---|---|---|
| • | • | • | • |
| • | • | • | • |
| • | • | • | • |

Female only: obstetrical history

| Date | Birth Weight | Date | Birth Weight |
|---|---|---|---|
| • | • | • | • |
| • | • | • | • |

As shown below, Table 2 shows the period of time moisture was being monitored and the number of positive reading of moisture readings by each sensor over a first test period. The first test period may be performed before an intervention in order to develop a baseline understanding of an individual's incontinence pattern.

TABLE 2

Baseline Period: Moisture Monitor Data

| Sensor | Total Hours Monitored | No Moistures: % of Hours (# of hours) | Some Moisture: % of Hours (# of hours) |
|---|---|---|---|
| • A | • | • | • |
| • B | • | • | • |
| • (list all) | • | • | • |

As shown below, Table 3 provides information regarding the user 010 and the period of time over which the data collection unit was activated over a second test period. The second test period may occur after an intervention has been implemented for an individual to evaluate the effectiveness of the intervention.

TABLE 3

Follow-up Period Moisture Monitor Data

| Sensor | Total Hours Monitored | No Moistures: % of Hours (# of hours) | Some Moisture: % of Hours (# of hours) |
|---|---|---|---|
| • A | • | • | • |
| • B | • | • | • |
| • (list all) | • | • | • |

As shown below, Table 4A provides comparison data between data collected during the first and second test periods.

TABLE 4A

Comparison of Follow-up Period with Baseline Period over 24-Hour Period

| Sensor | No Moisture: % of Hours | Some Moisture: % of Hours |
|---|---|---|
| • A | | |
| Baseline period | | |
| Evaluation period | | |
| % change | | |
| • B | • | • |
| Baseline period | | |
| Evaluation period | | |
| % change | | |
| • (list all sensors) | | |
| Baseline period | | |
| Evaluation period | | |
| % change | | |

As shown below, Table 4B provides an hour by hour comparative output of the data collected during the first and second test periods. This comparison may be used to assess any changes in an incontinence pattern, such as a change caused by an intervention. One skilled in the art will recognize that the compared data may be shown in a variety of other ways, for example in graphical form.

TABLE 4B

| Comparison of Follow-up Period with Baseline Period over 24-Hour Period* | | | | | | | | | | | | | | | | | | | | | | | | |
|---|---|---|---|---|---|---|---|---|---|---|---|---|---|---|---|---|---|---|---|---|---|---|---|---|
| | AM | | | | | | | | | | | | PM | | | | | | | | | | | | |
| | 12 | 1 | 2 | 3 | 4 | 5 | 6 | 7 | 8 | 9 | 10 | 11 | 12 | 1 | 2 | 3 | 4 | 5 | 6 | 7 | 8 | 9 | 10 | 11 | 12 |
| A | D | D | D | M | M | M | D | D | D | D | D | D | D | D | D | M | M | D | D | D | M | M | D | D |
| B | D | D | D | M | M | M | M | M | D | D | D | D | D | D | D | M | M | M | M | D | D | M | M | M |
| X | | | | | | | | | | | | | | | | | | | | | | | | |
| | 12 | 1 | 2 | 3 | 4 | 5 | 6 | 7 | 8 | 9 | 10 | 11 | 12 | 1D | 2 | 3 | 4 | 5 | 6 | 7 | 8 | 9 | 10 | 11 | 12 |

*Note:
"D" = dry interval; "M" = moisture present interval

Given the above description it should be appreciated that the disclosed stacked moisture sensing device 100 is able to provide quantitative data over an extended period of time during activities of daily living or in a hospital setting that can be used to identify and evaluate individuals who may be suffering from urinary incontinence related conditions. Other applications exist for the stacked moisture sensing device 100 in the shipping industry where increased monitoring can be attained which thereby will potentially increase product quality.

The above are example principles. Many embodiments can be made.

We claim:

1. A urinary continence monitoring system comprising:
   a. at least one stacked moisture sensing device comprising:
      i. a first media-sensor arrangement comprising:
         1. a first media layer having a first face, a second face, and a side edge extending between the first and second faces, the first media layer having a first hydrophilicity;
         2. a first moisture sensor embedded within the first media layer, the first moisture sensor being adapted to produce a first electrical signal when exposed to moisture;
      ii. a second media-sensor arrangement comprising:
         1. a second media layer having a first face, a second face and a side edge extending between the first and second faces, the second media layer having a second hydrophilicity different than the first hydrophilicity; and
         2. a second moisture sensor, separate from the first moisture sensor, embedded within the second media layer, the second moisture sensor being adapted to produce a second electrical signal, independent from the first electrical signal, when exposed to moisture;
         3. wherein the second media-sensor arrangement is stacked upon the first media-sensor arrangement; and
   b. an absorbent undergarment having a pass through layer and an absorbent layer;
   c. wherein the absorbent undergarment further comprises indicia, separate from the stacked moisture sensing device, for identifying the location of where the at least one stacked moisture sensing device is to be located on the absorbent undergarment.

2. The urinary continence monitoring system of claim 1, wherein the indicia is in the form of an indicia pattern for identifying the locations of a plurality of stacked moisture sensing devices.

3. The urinary continence monitoring system of claim 2, wherein the indicia pattern is based upon at least one of a gender of a user and an anticipated primary position of the user.

4. The urinary continence monitoring system of claim 2, wherein the indicia comprises multiple indicia patterns.

5. The urinary continence monitoring system of claim 4, wherein the indicia patterns are based upon the primary position of a user.

* * * * *